(12) United States Patent
Kuo et al.

(10) Patent No.: US 8,547,549 B2
(45) Date of Patent: Oct. 1, 2013

(54) SUBSTRATE FOR SURFACE ENHANCED RAMAN SCATTERING (SERS)

(75) Inventors: Huei Pei Kuo, Cupertino, CA (US); Jing Tang, Menlo Park, CA (US); Fung Suong Ou, Houston, TX (US); Zhiyong Li, Redwood City, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 193 days.

(21) Appl. No.: 13/129,571

(22) PCT Filed: Nov. 17, 2008

(86) PCT No.: PCT/US2008/083827
§ 371 (c)(1),
(2), (4) Date: May 16, 2011

(87) PCT Pub. No.: WO2010/056258
PCT Pub. Date: May 20, 2010

(65) Prior Publication Data
US 2011/0228266 A1    Sep. 22, 2011

(51) Int. Cl.
*G01J 3/44*    (2006.01)
*G01N 21/65*    (2006.01)

(52) U.S. Cl.
USPC ........................................................ 356/301

(58) Field of Classification Search
USPC ........................................................ 356/301
See application file for complete search history.

(56) References Cited

U.S. PATENT DOCUMENTS

| | | | |
|---|---|---|---|
| 7,158,219 B2 * | 1/2007 | Li et al. | 356/36 |
| 7,224,451 B2 | 5/2007 | Naya | |
| 7,236,242 B2 * | 6/2007 | Kamins et al. | 356/301 |
| 7,288,419 B2 | 10/2007 | Naya | |
| 7,351,588 B2 | 4/2008 | Poponin | |
| 7,388,661 B2 * | 6/2008 | Li et al. | 356/301 |
| 7,426,025 B2 * | 9/2008 | Wang | 356/301 |
| 7,476,787 B2 | 1/2009 | Thomas et al. | |
| 7,576,854 B2 | 8/2009 | Wang | |
| 7,586,601 B2 | 9/2009 | Ebstein | |
| 7,609,378 B2 | 10/2009 | Konakahara | |
| 7,651,863 B2 * | 1/2010 | Hulteen et al. | 436/165 |
| 7,656,525 B2 | 2/2010 | Zhao | |
| 7,707,647 B2 | 4/2010 | Konakahara | |
| 7,965,388 B2 | 6/2011 | Xia et al. | |
| 8,294,891 B2 * | 10/2012 | Mazur et al. | 356/301 |

(Continued)

FOREIGN PATENT DOCUMENTS

| | | |
|---|---|---|
| JP | 2005-524857 A | 12/2003 |
| JP | 2006-349463 A | 12/2006 |

(Continued)

OTHER PUBLICATIONS

Application (PCT/US2008/083827).

(Continued)

*Primary Examiner* — Layla Lauchman (57) ABSTRACT

A substrate for Surface Enhanced Raman Scattering (SERS). The substrate comprises at least one nanostructure protruding from a surface of the substrate and a SERS active metal over the at least one nanostructure, wherein the SERS active metal substantially covers the at least one nanostructure and the SERS active metal creates a textured layer on the at least one nanostructure.

14 Claims, 7 Drawing Sheets

(56) References Cited

U.S. PATENT DOCUMENTS

| | | | |
|---|---|---|---|
| 2001/0006869 | A1 | 7/2001 | Okamoto et al. |
| 2003/0201717 | A1 | 10/2003 | Hibino et al. |
| 2004/0135997 | A1 | 7/2004 | Chan et al. |
| 2006/0250613 | A1 | 11/2006 | Demuth et al. |
| 2007/0015288 | A1 | 1/2007 | Hulteen et al. |
| 2007/0086001 | A1 | 4/2007 | Islam |
| 2007/0115469 | A1 | 5/2007 | Ebstein et al. |
| 2008/0079104 | A1 | 4/2008 | Stewart et al. |
| 2008/0094621 | A1 | 4/2008 | Li |
| 2009/0117646 | A1 | 5/2009 | Stordeur |
| 2010/0062226 | A1 | 3/2010 | Hulteen |
| 2010/0321684 | A1 | 12/2010 | Bratkovski |
| 2012/0013903 | A1 | 1/2012 | Kuo |
| 2012/0113419 | A1 | 5/2012 | Wang |

FOREIGN PATENT DOCUMENTS

| | | |
|---|---|---|
| JP | 2007-240361 A | 9/2007 |
| JP | 2008-035874 A | 2/2008 |
| WO | WO-2006/132224 | 12/2006 |
| WO | WO-2006138442 | 12/2006 |
| WO | WO-2007/011671 | 1/2007 |
| WO | WO-2010056258 | 5/2010 |
| WO | WO-2011014176 | 2/2011 |

OTHER PUBLICATIONS

Application (PCT/US2009/052308).

Cao, et al., "Enhance Raman Scattering from Individual Semiconductor Nanocones and Nanowires", Physical Review Letters PRL 96, 157402, 2006.

Gilles, et al., "UV Nanoimprint Lithography with Rigid Polymer Molds", Microelectronic Engineering 86, (2009), pp. 661-664.

He, et al., "Large-Scale Synthesis of Flexible Free-Standing SERS Substrates with High Sensitivity: Electrospun PVA Nanofibers Embedded with Controlled Alignment of Silver Nanoparticlels" ACSNANO vol. 3, No. 12, 3993-4002, (2009).

Hu, et al., "Metal Coated Si Nanograss as Highly Sensitive SERS Sensors", Proc. of SPIE, vol. 7312, (2009), pp. 73120I-1-6.

PCT Search Report, PCT/US2008/083827 (82248926).

PCT Search Report, PCT/US2009/052308 (82258109).

Schmidt, et al., "Towards Easily Reproducible Nano-Structured SERS Substrates", IEEE Sensors 2009 Conference, (2009), pp. 1763-1767.

Wu, et al., "One-Kilobit Cross-Bar Molecular Memory Circuits at 30-nm Half- Pitch Fabricated by Nanoimprint Lithography", Springer-Verlag, Pub online, (Mar. 11, 2005), 1173-1178.

\* cited by examiner

SUBSTRATE FOR SURFACE ENHANCED RAMAN SCATTERING (SERS)

STATEMENT OF GOVERNMENT INTEREST

This invention has been made with Government support under Contract No. HR0011-09-3-0002, awarded by the Defense Advanced Research Projects Agency. The government has certain rights in the invention.

FIELD

Embodiments of the present technology relates generally to the field of nanotechnology.

BACKGROUND

Surface Enhanced Raman Scattering (SERS) is a technique using Raman scattering for enhancing the detection of molecular species through the excitation of Plasmon modes and their coupling to molecular vibrational modes. In other words, Raman scattering is the inelastic scattering of photons that can provide vibrational fingerprints of molecules. The substrate surface on which the detection of molecular species is taking place, as well as the material of the substrate surface affects the strength and intensity of the Raman scattering.

Currently available substrates for use in SERS suffer from various deficiencies in the enhancement and detection of Raman scattering. Raman scattering signals are generally very weak, especially on flat substrates. The weak Raman signal can make it difficult to detect and measure the Raman scattering signal and consequently make it difficult to detect and identify the molecular species. Furthermore, even if the available substrate enhances the Raman scattering signal, the enhanced Raman scattering signal is usually in a localized area(s) on the substrate and not uniform across the substrate surface. The area of the localized enhanced Raman scattering signal is exponentially small compared to the entire area of the substrate surface. The large disparity between the area of the Raman scattering signal and the area of the substrate surface make it burdensome to search and locate the signal and consequently burdensome to detect and identify the molecular species.

Moreover, current substrates are expensive and difficult to manufacture. The manufacturing of the substrates can require burdensome and expensive lithographically patterned masking and etch-stopping layers. The lithography process also limits the density of the features on the substrate surface that enhances Raman scattering and thus the intensity of the observed Raman signal.

BRIEF DESCRIPTION OF THE DRAWINGS

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

The surface of a substrate for the use in SERS can influence the Raman signal, as described above. The shape and size of the physical features on the substrate surface as well as the material of the physical features can amplify the Raman signal to help detect and identify molecules located at or near the substrate surface. In particular, light is directed at the substrate surface and the reflected light has a signature that identifies the molecules located at or near the substrate surface.

Figure 1A:
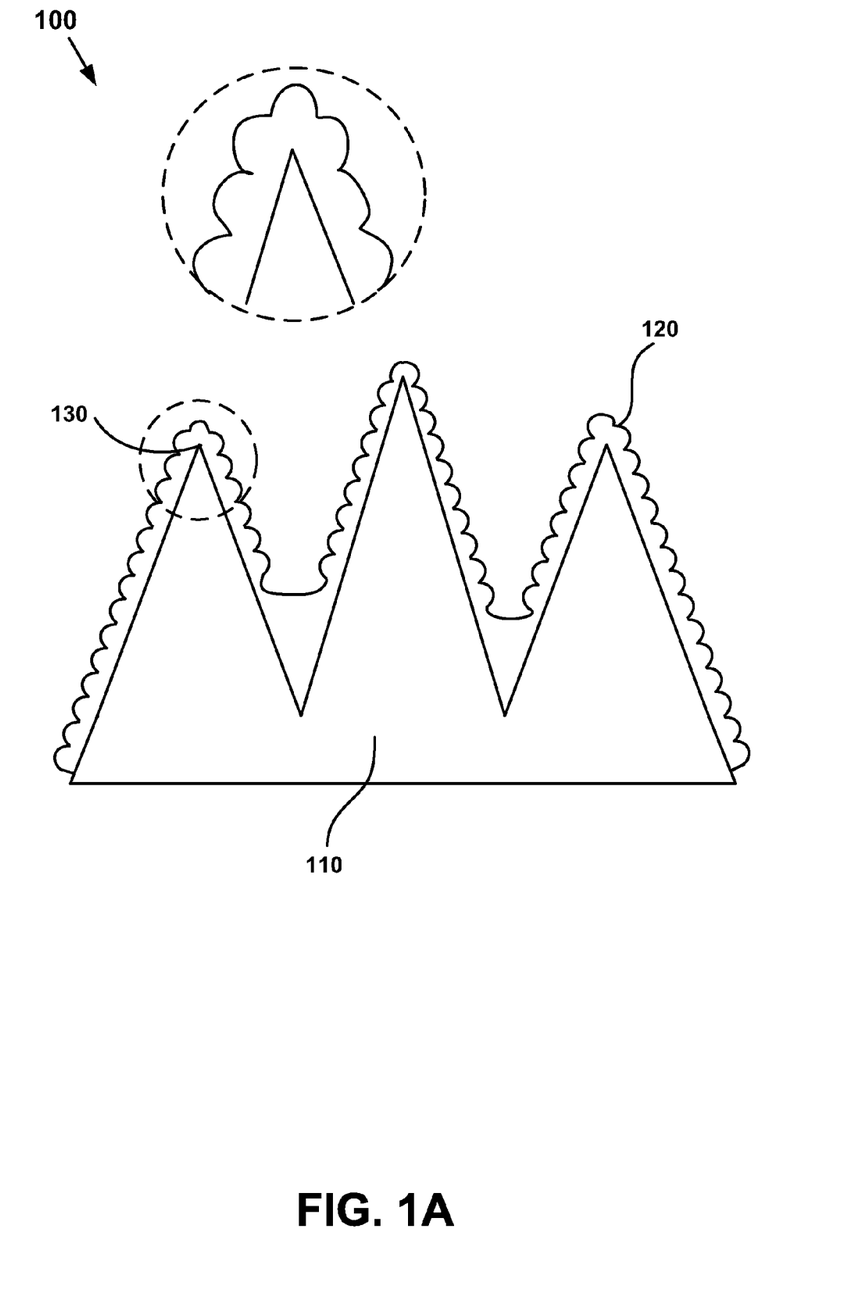
FIG. 1a illustrates an example of a substrate with a SERS active metal over nanostructures, in accordance with an embodiment of the present invention.

FIG. 1a illustrates an example of a cross-sectional view of a substrate 100, for the use in SERS to detect and identify molecules. The substrate 100 has nanostructures 110 protruding from a surface of the substrate. The nanostructures 110 have a tip portion 130. A layer of metal 120 is formed over the nanostructures 110. The layer of metal 120 provides a textured surface over the nanostructures. The textured surface can be, but is not limited to, a bumpy, wavy or rough surface. The layer of metal 120 and the textured surface is generally uniform. The process(es) used to apply the layer of metal over the nanostructure, described later, allows for a varying and random textured surface. In various embodiments, the metal 120 includes at least one SERS active metal. SERS active metals can be, but are not limited to, silver, gold, platinum or copper. SERS active metals are metals that help provide for the enhancement of Raman scattering during SERS. In one embodiment, only one nanostructure protrudes from a surface of the substrate. In one embodiment, the shank of the nanostructure can be macroscopic and the tip of the protrusion is a nanostructure. In another embodiment, the substrate and the protrusion is one single needle-like structure with a radius of curvature of the needle point having a range of, but not limited to 10 to 1000 nm.

In one embodiment, the thickness of the layer of SERS active metal 120 can be, but is not limited to, the range of 10 nm to 120 nm. In another embodiment, the thickness of the layer of SERS active metal is 80 nm.

Figure 1B:
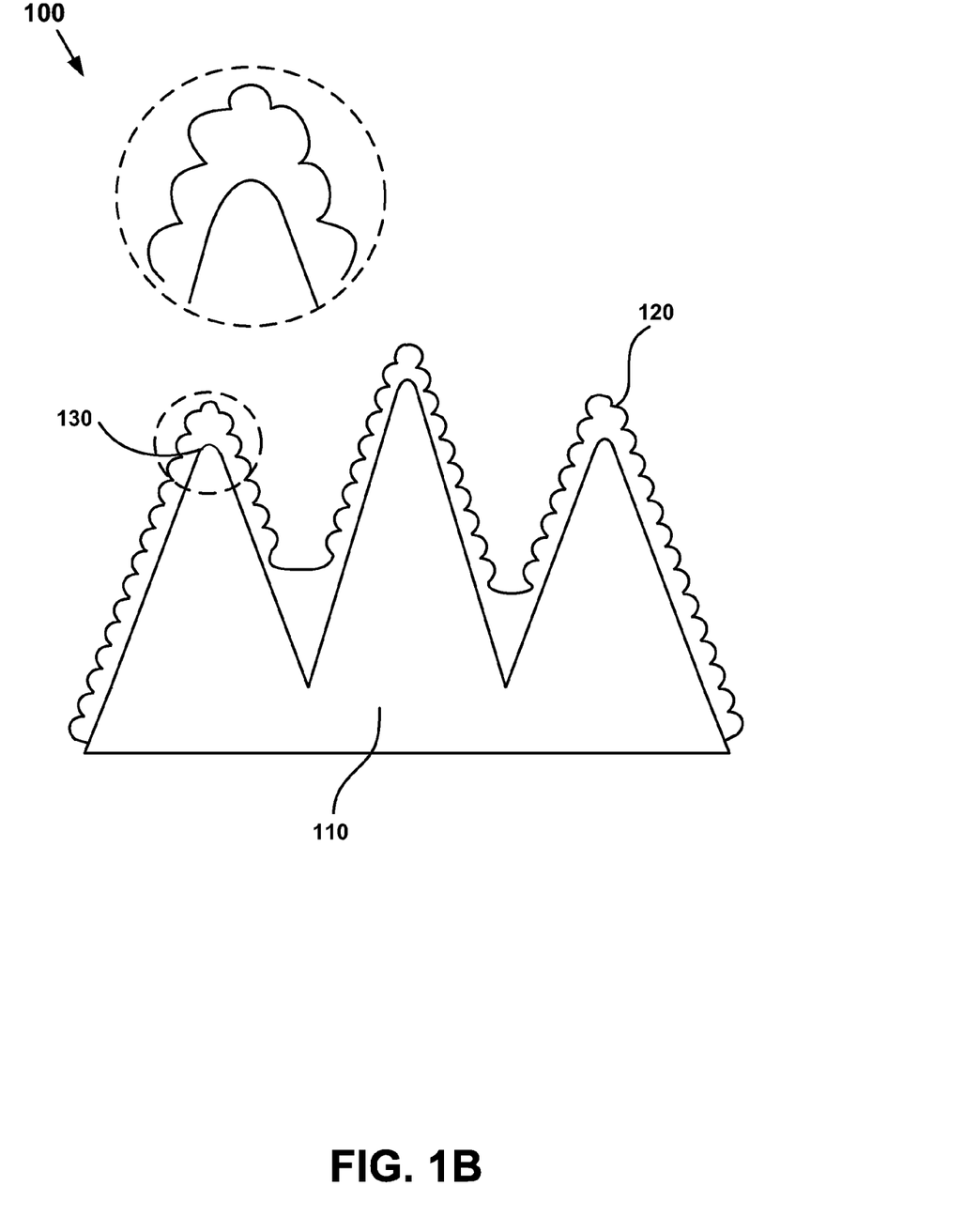
FIG. 1b illustrates an example of a substrate with a SERS active metal over nanostructures, in accordance with an embodiment of the present invention.
Figure 1C:
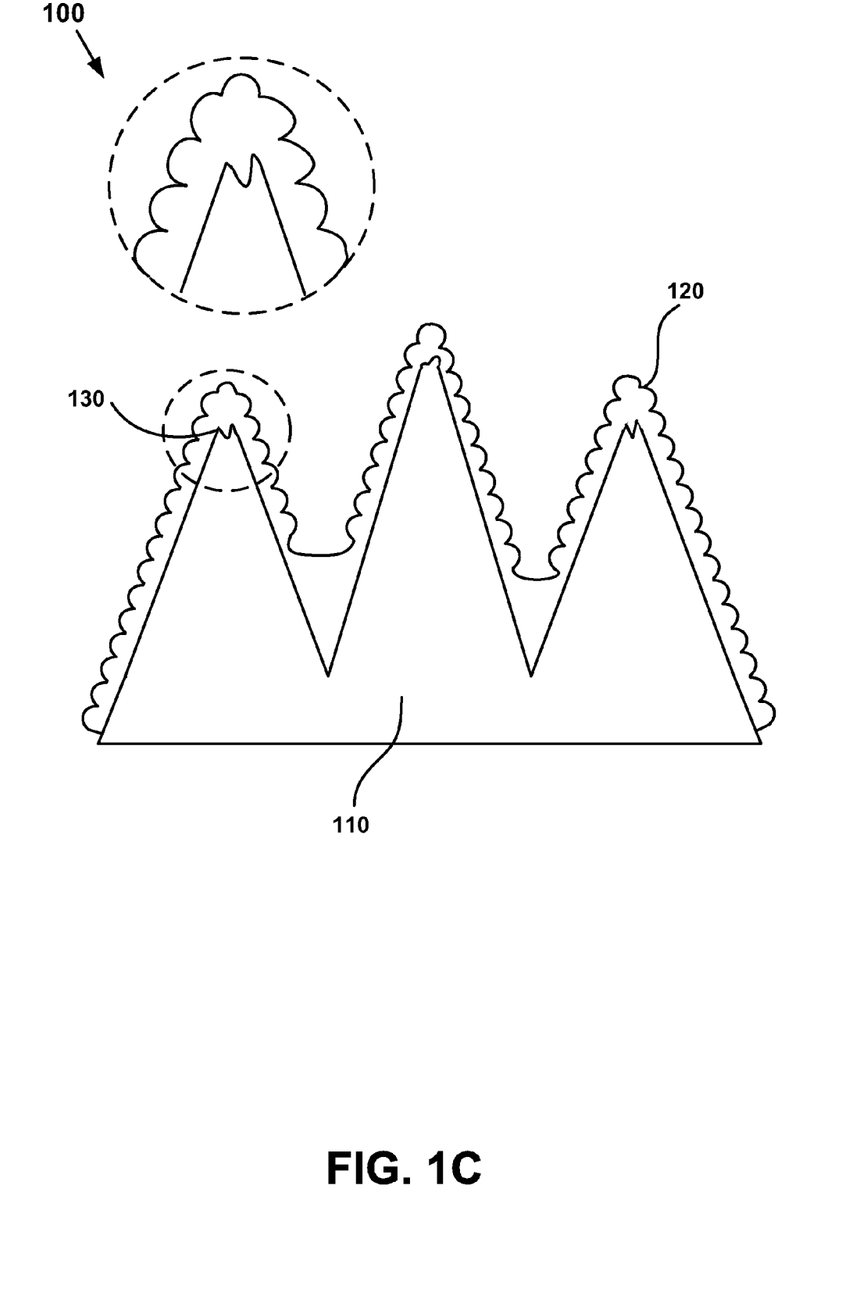
FIG. 1c illustrates an example of a substrate with a SERS active metal over nanostructures, in accordance with an embodiment of the present invention.

In one embodiment, the nanostructures 110 are generally a conical shape. In various embodiments, the shapes of the nanostructures 110 are not limited to hemispheres, pyramids or amorphous. FIG. 1a illustrates a cross-sectional view of a substantially cone-shaped or a substantially pyramid shape nanostructure. For the sake of clarity, tip portion 130 has been expanded to show further detail. FIG. 1b illustrates a substantially hemisphere shaped tip of the nanostructure. For the sake of clarity, tip portion 130 has been expanded to show further detail. FIG. 1c illustrates a substantially amorphous shaped tip of the nanostructure. For the sake of clarity, tip portion 130 has been expanded to show further detail. The process used to fabricate the nanostructure 110, described later, allows for the variations of the nanostructures. The variations of the nanostructures can be, but are not limited to shape, width, height and density. The height of a cone can be, but is not limited to, one micron.

The density of the nanostructures 110 on the substrate 100 is substantially uniform across the surface of the substrate. The distance between the cone tips can be, but is not limited to, a range of 100 nm to 500 nm. In one embodiment, the distance between the cone tips is sub-wavelength. In another embodiment, the distance is in a range of wavelength to sub-wavelength. The bases of the nanostructures can be proximate one another. In one embodiment, the bases of the nanostructures are not proximate. In a further embodiment, the bases of a plurality of nanostructures are proximate one another and bases of another plurality of nanostructures are not proximate one another.

Figure 2:
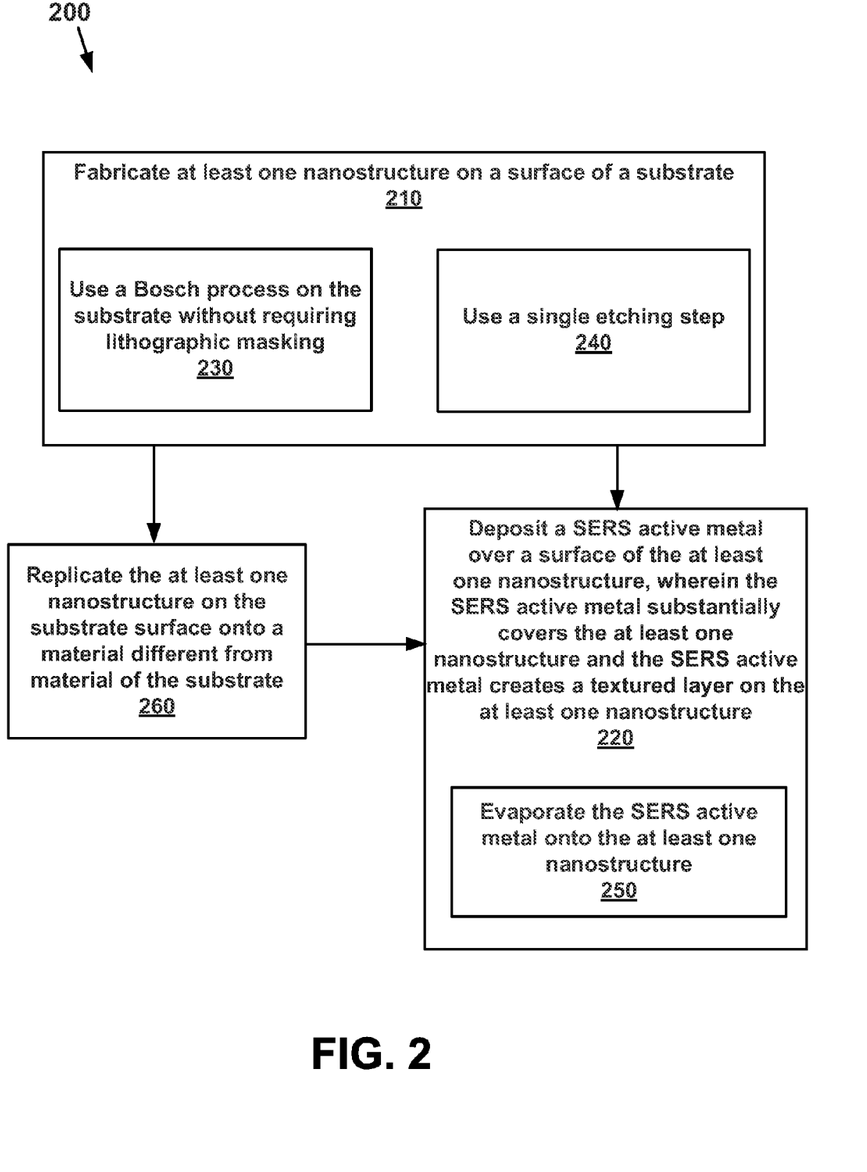
FIG. 2 illustrates an example of a flow chart of a method of manufacturing a substrate with nanostructures, in accordance with an embodiment of the present invention.

FIG. 2 illustrates the method 200 of manufacturing a substrate for the use in SERS. At block 210, at least one nanostructure is fabricated on a surface of the substrate. In one embodiment, the fabrication is performed using a customized Bosch process. In one embodiment, the Bosch process can be performed on a single crystalline silicon. In another embodiment, the fabrication is done in a single etching step. In another embodiment, the fabrication is done without a lithographically patterned masking layer. In another embodiment, only one nanostructure is fabricated.

At block 230, the fabricating of the nanostructures can be performed using a customized Bosch process on the substrate without requiring lithographic masking. At block 240, the fabricating of the nanostructures can be performed using a single etching step.

Figure 3A:
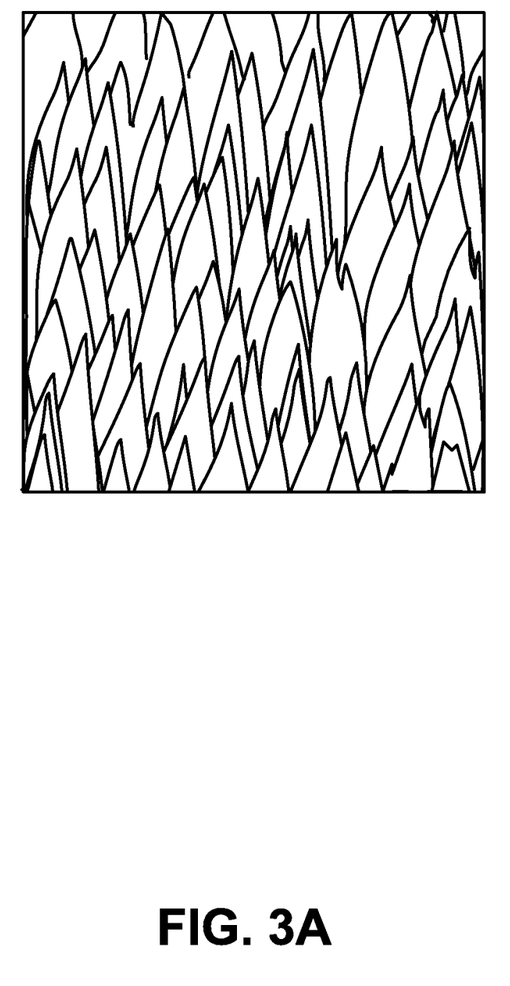
FIG. 3a illustrates an example of nanostructures, in accordance with an embodiment of the present invention.
Figure 3B:
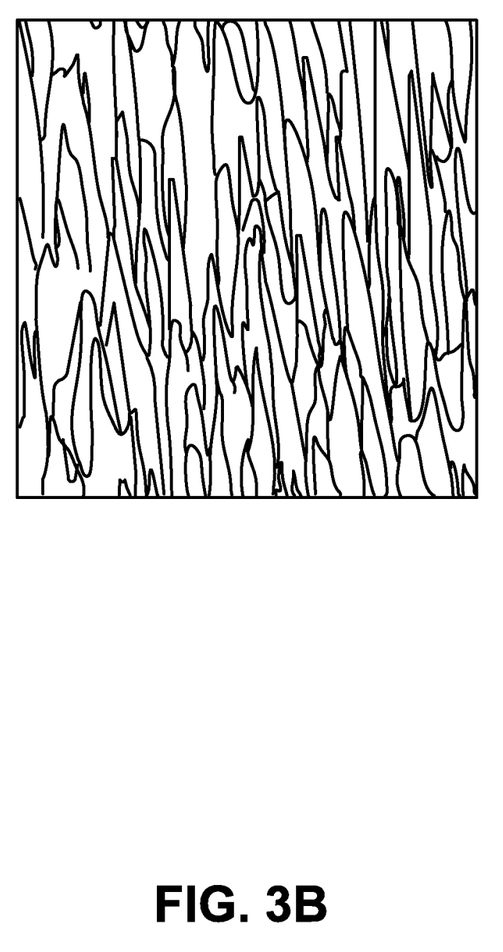
FIG. 3b illustrates an example of nanostructures, in accordance with an embodiment of the present invention.

The surface structure of the SERS substrate varies as a function of etching time. In particular, the height of the nanostructures increases as the time of etching increases. FIG. 3a illustrates an example of the nanostructures of a SERS substrate, before metal deposition, after 550 seconds of etching. FIG. 3b illustrates another example of the nanostructures of a SERS substrate, before metal deposition, after 20 minutes of etching. The fabricated nanostructures are self-organized. In one embodiment, the nanostructures are randomly fabricated on the substrate. In another embodiment, the nanostructures are densely packed on the substrate. In a further embodiment, the nanostructures have an appearance of a bed-of-nails. In another embodiment, the nanostructures have an appearance similar to trees in a forest.

Figure 3C:
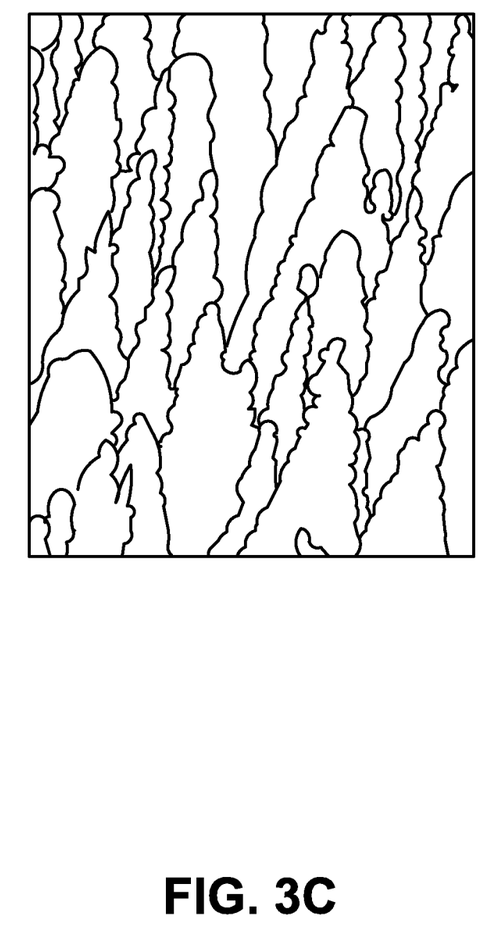
FIG. 3c illustrates an example of SERS active metal over nanostructures, in accordance with an embodiment of the present invention.

At block 220, a SERS active metal is deposited over a surface of the nanostructures. The SERS active metal substantially covers the nanostructures and creates a textured layer on the nanostructures. FIG. 3c illustrates one embodiment of the SERS active metal over the nanostructures. In particular, FIG. 3c depicts a silicon substrate with a 9 minute etching and 80 nm of silver (Ag) deposited over the conical nanostructures. In another embodiment, the SERS active metal can be evaporated over the nanostructures. In a further embodiment, the SERS active metal can be chemically deposited over the nanostructures. In one embodiment, the SERS active metal is chemically deposited by the process of plating. Furthermore, the SERS active metal can be deposited over the nanostructure by a pre-assembled nanostructure coating. The pre-assembled nanostructure coating can be a pre-synthesized metal that is then deposited over the nanostructures. In one embodiment, the deposition of the SERS active metal does not require masking. In another embodiment, the deposition of the SERS active metal does not require lithography processes. In another embodiment, there is post processing after the deposition of metal. At block 250, the SERS active metal can be evaporated onto the nanostructures.

At block 260, the surface of the substrate with the fabricated nanostructures can be replicated. The desire to replicate the substrate surface having nanostructures is to provide a wide-variety of low cost SERS substrates. In one embodiment, the replicating of substrate with fabricated nanostructures does not require an etching process. In one embodiment, the surface of the substrate with fabricated nanostructures can be replicated on a material different than the material of the substrate. In another embodiment, the surface of the substrate with fabricated nanostructures can be replicated on a material that is the same as the material of the substrate.

In one embodiment, the original substrate surface with nanostructures is used as a master mold. In one embodiment, the replicating can be achieved by embossing. In another embodiment, a layer of polymer can be applied to the substrate surface and the polymer is subsequently peeled off the substrate surface. The peeled off polymer is then used as SERS substrate having a plurality of nanostructures. In various embodiments, the replicating is achieved by but not limited to stamping, thermal embossing or UV curing. In a further embodiment, the replicating of a substrate with nanostructures does not require an etching process. In one embodiment, the replicating of a substrate with nanostructures does not require a vacuum process. In another embodiment, a positive mold is used for replicating. In a further embodiment, a negative mold is used for replicating. In a further embodiment, the original substrate with nanostructures can be impressed into a replicating material to a range of depth of 500 nm or less. In another embodiment, the original substrate with nanostructures can be impressed into a replicating material to a range of depth of 100 nm or less. For example, the replicated material can be, but is not limited to, plastic, thermal plastic, acrylic, UV curable material or metal. It should be appreciated that any material capable of maintaining structures at a nanometer scale can be used as the replicating material.

The material for the replicated substrate surface with nanostructures can be any material that allows for the replication of the substrate surface with nanostructures. The material for the replicated substrate surface with nanostructures is not limited to silicon. In another embodiment, the material for the replicated substrate surface with nanostructures is different than the original substrate material. In one embodiment, the material for the replicated substrate surface with nanostructures is the same as the original substrate material. For example, the material for the replicated substrate surface with nanostructures can be the same as the original substrate material by the use of a release layer.

After the substrate surface with nanostructures is replicated, as described at block 260, a SERS active metal is deposited over a surface of the replicated nanostructures, as described at block 220. In one embodiment, the SERS active metal can be evaporated over the replicated nanostructures. In a further embodiment, the SERS active metal can be chemically deposited by over the replicated nanostructures. In one embodiment, the SERS active metal is chemically deposited by the process of plating. Furthermore, the SERS active metal can be deposited over the replicated nanostructures by a pre-assembled nanostructure coating. The pre-assembled nanostructure coating can be a pre-synthesized metal that is then deposited over the replicated nanostructures. In one embodiment, the deposition of the SERS active metal does not require masking. In another embodiment, the deposition of the SERS active metal does not require lithography processes. In another embodiment, there is post processing after the deposition of metal.

The substrate used and nanostructures can have their statistical, mechanical, chemical and optical properties tailored by varying the starting material, etching and deposition parameters. In one embodiment, dopants, such as but not limited to N and P, can affect the conductivity and thus the plasmonic structures of the nanostructured surfaces of the substrates. Dopants can also affect the electromagnetic field enhancement on Raman scattering.

The depth of the height of the nanostructures can be controlled by silicon-on-sapphire (SOS) structures and/or silicon-on-insulator (SOI) structures. The SOS and/or SOI structures provide etch stops to help control the height of the nanostructures. The time of etching, as described above, also controls the height of the nanostructures. Etching can also control and optimize the profiles, density and distribution of the nanostructures on the substrate surface. The control parameters of the etching can be but are not limited to Bosch process, time steps, gas flow or power. Planarization and etch can also provide an independent control of the height of the nanostructures on the substrate surface.

The SERS active metals deposited over the nanostructures can optimize the field enhancement and stability of the substrates. Control parameters of the deposition can be but are not limited to the materials, thickness, rate or surface finish.

As described above, currently available SERS substrates can require patterned masking and etch-stopping layers. The masking and etch-stopping layers make the substrate expensive and limits the density of the sites that enhances the Raman signal. The limitations of the substrate surface provides for a weak Raman signal that can make it difficult to detect and measure the Raman scattering signal and make it difficult to detect and identify the molecular species. Moreover, even if the available substrate enhances the Raman scattering signal, the enhanced Raman scattering signal is usually in a localized area(s) on the substrate and not uniform across the substrate surface. The large disparity between the area of the Raman scattering signal and the area of the substrate surface make it burdensome to search and locate the signal and consequently burdensome to detect and identify the molecular species. In order to find the Raman scattering signal, a microscope or the like is used to find the weak signal in a localized area. The process to find the Raman scattering signal can be quite burdensome and time consuming.

Compared to currently available SERS substrates, in one embodiment, the Raman signal is enhanced by a factor of 7. The wave length of the pumping light source was 785 nm. In another embodiment, the Raman signal is enhanced by a factor of 5 compared to a currently available SERS substrate. The wave length of the pumping light source was 632 nm. In another embodiment, the Raman signal is increased by over 10 times compared to a currently available SERS substrate. In one embodiment, compared to a flat substrate, the SERS signal is enhanced by a factor of $10^7$.

The nanostructures fabricated on the surface of the substrate have a uniform density across the surface of the substrate. In one embodiment, the uniform density of the nanostructures provides for a uniform and reliable enhanced Raman scattering signal across the surface of the substrate. In another embodiment, the area of uniform density of nanostructures is greater than 100 cm$^2$. In a further embodiment, the area of a uniform and reliable Raman scattering signal is greater than 100 cm$^2$. In one embodiment, searching for the Raman scattering is not required because the enhanced Raman scattering signal is uniform and reliable across the substrate surface. In another embodiment, the substrate is a large-area nanostructured substrate that exhibits consistently repeatable strong enhancement of Raman scattering over the substrate.

Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims

The invention claimed is:

1. A substrate for Surface Enhanced Raman Scattering (SERS), said substrate comprising:
    at least one nanostructure protruding from a surface of said substrate, wherein said at least one nanostructure comprises:
        an amorphous tip portion; and
        a macroscopic shank portion; and
    a SERS active metal over said at least one nanostructure, wherein said SERS active metal substantially covers said at least one nanostructure and said SERS active metal creates a textured layer on said at least one nanostructure.

2. The substrate of claim 1, wherein said at least one nanostructure has a shape that is selected from a list consisting essentially of: substantially cone-shaped, hemisphere, pyramid or amorphous shape.

3. The substrate of claim 1, wherein said at least one nanostructure is randomly distributed onto said substrate.

4. The substrate of claim 1, wherein said substrate comprises a plurality of nanostructures and said plurality of nanostructures have a substantially uniform density across said substrate surface.

5. The substrate of claim 1, wherein Raman Scattering is substantially uniform across said substrate surface.

6. The substrate of claim 1, wherein said SERS active metal is selected from a list consisting essentially of: silver, gold, platinum and copper.

7. A method of manufacturing a substrate for Surface Enhanced Raman Scattering (SERS), said method comprising:
    fabricating at least one nanostructure on a surface of said substrate, wherein said at least one nanostructure comprises an amorphous tip portion, and a macroscopic shank portion; and
    depositing a SERS active metal over said at least one nanostructure, wherein said SERS active metal substantially covers said at least one nanostructure and said SERS active metal creates a textured layer on said at least one nanostructure.

8. The method of claim 7, wherein said fabricating is performed using a Bosch process on said substrate without requiring lithographic masking.

9. The method of claim 7, wherein said fabricating is performed using a single etching step.

10. The method of claim 7, wherein said depositing comprises evaporating said SERS active metal over said at least one nanostructure.

11. The method of claim 7, wherein said at least one nanostructure is self-organized.

12. The method of claim 7, wherein said fabricating comprises replicating said at least one nanostructure on said substrate surface onto another substrate.

13. The method of claim 12, wherein said replicating does not require an etching process.

14. A substrate for Surface Enhanced Raman Scattering (SERS), said substrate comprising:
- a plurality of nanostructures protruding from a surface of said substrate, wherein said plurality of nanostructures are substantially cone-shaped, said plurality of nanostructures have a substantially uniform density and are randomly distributed across said substrate surface, wherein said at least one of said plurality of nanostructures comprises:
  - an amorphous tip portion; and
  - a macroscopic shank portion; and
- a SERS active metal evaporated over said plurality of nanostructures, wherein said SERS active metal substantially covers said plurality of nanostructures and said SERS active metal creates a textured layer on said plurality of nanostructures, such that Raman scattering is substantially uniform across said substrate surface.

* * * * *